US008002786B2

(12) United States Patent
Beckman et al.

(10) Patent No.: US 8,002,786 B2
(45) Date of Patent: *Aug. 23, 2011

(54) HAND ASSISTED LAPAROSCOPIC SEAL ASSEMBLY WITH DEFLECTION FEATURE

(75) Inventors: Andrew T. Beckman, Cincinnati, OH (US); Mark J. Reese, Cincinnati, OH (US); Michael D. Cronin, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 442 days.

This patent is subject to a terminal disclaimer.

(21) Appl. No.: 11/716,029

(22) Filed: Mar. 9, 2007

(65) Prior Publication Data

US 2008/0221389 A1    Sep. 11, 2008

(51) Int. Cl.
*A61B 1/00* (2006.01)

(52) U.S. Cl. .................................................... 606/184

(58) Field of Classification Search ............... 606/201, 606/203, 204, 206, 208, 210, 108; 90/215, 90/216, 230; 220/86.2; 74/575, 577 S, 527–531, 74/502.2, 489; 215/216, 230; 604/513, 167.02; 600/184, 201, 203, 204, 206, 208, 210, 108
See application file for complete search history.

(56) References Cited

U.S. PATENT DOCUMENTS

| | | | |
|---|---|---|---|
| 4,094,492 A | 6/1978 | Beeman et al. | |
| 4,775,074 A * | 10/1988 | Ershig | 220/323 |
| 5,266,066 A * | 11/1993 | White | 474/111 |
| 5,449,141 A | 9/1995 | Gillett et al. | |
| 5,524,501 A * | 6/1996 | Patterson et al. | 74/473.25 |
| 5,640,977 A | 6/1997 | Leahy et al. | |
| 5,921,140 A * | 7/1999 | Lemmens | 74/473.28 |
| 6,578,577 B2 | 6/2003 | Bonadio et al. | |
| 6,589,167 B1 * | 7/2003 | Shimomura et al. | 600/208 |
| 7,052,454 B2 | 5/2006 | Taylor | |
| 7,153,261 B2 * | 12/2006 | Wenchell | 600/208 |
| 7,300,399 B2 * | 11/2007 | Bonadio et al. | 600/208 |
| 7,393,322 B2 * | 7/2008 | Wenchell | 600/208 |
| 7,540,839 B2 | 6/2009 | Butler et al. | |
| 7,559,893 B2 | 7/2009 | Bonadio et al. | |
| 7,678,046 B2 * | 3/2010 | White et al. | 600/184 |
| 7,766,822 B2 | 8/2010 | White et al. | |
| 2002/0072762 A1 | 6/2002 | Bonadio et al. | |
| 2004/0073090 A1 | 4/2004 | Butler et al. | |
| 2004/0092795 A1 | 5/2004 | Bonadio et al. | |
| 2004/0154624 A1 | 8/2004 | Bonadio et al. | |
| 2005/0020884 A1 | 1/2005 | Hart et al. | |
| 2005/0155611 A1 | 7/2005 | Vaugh et al. | |
| 2005/0192483 A1 | 9/2005 | Bonadio et al. | |
| 2005/0222582 A1 * | 10/2005 | Wenchell | 606/108 |
| 2005/0241647 A1 * | 11/2005 | Nguyen et al. | 128/856 |
| 2006/0084842 A1 * | 4/2006 | Hart et al. | 600/206 |
| 2006/0149306 A1 * | 7/2006 | Hart et al. | 606/191 |
| 2006/0161050 A1 | 7/2006 | Butler et al. | |
| 2006/0247500 A1 | 11/2006 | Voegele et al. | |
| 2007/0055107 A1 * | 3/2007 | Wenchell | 600/208 |
| 2007/0185387 A1 * | 8/2007 | Albrecht et al. | 600/208 |

(Continued)

*Primary Examiner* — Todd E Manahan
*Assistant Examiner* — Christopher Schubert

(57) ABSTRACT

A seal assembly for permitting hand assisted laparoscopic procedures is disclosed. The seal assembly includes a seal cap having a seal positioned within a housing. The housing includes a lower seal ring having a track which supports an upper seal ring for relative rotational motion. The seal is supported between the upper seal ring and the lower seal ring for rotation between an open orientation and a closed orientation. A ratchet mechanism is provided for controlling motion of the upper seal ring relative to the lower seal ring. The ratchet mechanism includes a deflection feature and a series of gear teeth, wherein the series of gear teeth are oriented to engage the deflection feature.

17 Claims, 8 Drawing Sheets

U.S. PATENT DOCUMENTS

| | | |
|---|---|---|
| 2007/0272706 A1* | 11/2007 | Gilbertson et al. ............ 222/109 |
| 2008/0097163 A1* | 4/2008 | Butler et al. .................. 600/208 |
| 2008/0132765 A1* | 6/2008 | Beckman et al. ............. 600/204 |
| 2008/0146882 A1* | 6/2008 | Cropper et al. ............... 600/206 |
| 2008/0146883 A1* | 6/2008 | Kistler et al. ................. 600/207 |
| 2008/0146884 A1* | 6/2008 | Beckman et al. ............. 600/208 |
| 2008/0208175 A1 | 8/2008 | Beckman et al. |
| 2008/0208222 A1* | 8/2008 | Beckman et al. ............. 606/148 |
| 2008/0249371 A1 | 10/2008 | Beckman et al. |
| 2008/0249373 A1* | 10/2008 | Wenchell ...................... 600/208 |
| 2008/0284114 A1 | 11/2008 | Price et al. |
| 2009/0082632 A1 | 3/2009 | Voegele |

* cited by examiner

HAND ASSISTED LAPAROSCOPIC SEAL ASSEMBLY WITH DEFLECTION FEATURE

BACKGROUND OF THE INVENTION

1. Field of the Invention

The invention relates to laparoscopic devices. In particular, the invention relates to a laparoscopic seal assembly permitting the use of hands in assisting during laparoscopic procedures.

2. Description of the Related Art

During laparoscopic procedures, it is often desirable for the surgeon to place his or her hand within the patient in a manner manipulating the instruments positioned within the patient. When this occurs, it is desirable to separate the external environment from the internal portion of the patient. For example, when hand assisted laparoscopic procedures are performed within the abdominal cavity, it is desirable to perform hand exchanges with minimal loss of abdominal pressure. As such, a need exists for skin mountable seals permitting hand assisted laparoscopic procedures without fear that the abdominal pressure will be compromised. The present invention provides such an apparatus.

SUMMARY OF THE INVENTION

It is, therefore, an object of the present invention to provide a seal assembly for permitting hand assisted laparoscopic procedures. The seal assembly includes a seal cap with a seal positioned within a housing. The housing includes a lower seal ring having a track which supports an upper seal ring for relative rotational motion. The seal is supported between the upper seal ring and the lower seal ring for rotation between an open orientation and a closed orientation. A ratchet mechanism is provided for controlling motion of the upper seal ring relative to the lower seal ring. The ratchet mechanism includes a deflection feature and a series of gear teeth, wherein the series of gear teeth are oriented to engage the deflection feature.

It is also an object of the present invention to provide a seal assembly wherein the series of gear teeth is secured to the upper seal ring and the deflection feature is secured to the lower seal ring.

It is also another object of the present invention to provide a seal assembly wherein the upper seal ring includes a downwardly extending flange and the series of gear teeth is secured to the downwardly extending flange, and the lower seal ring includes an upwardly extending wall and the deflection feature is secured to the upwardly extending wall.

It is also a further object of the present invention to provide a seal assembly wherein the deflection feature is a spring fastener.

It is yet a further object of the present invention to provide a seal assembly wherein the spring fastener is a flat spring having a first end and a second end rigidly secured to the lower seal ring.

It is still a further object of the present invention to provide a seal assembly wherein the spring fastener includes a convex portion between the first end and the second end, and the convex portion is shaped and dimensioned to seat within the series of gear teeth as the upper seal ring and the lower seal ring are moved relative to each other.

It is also an object of the present invention to provide a seal assembly wherein the spring fastener is a flat spring having a first end and a second end, and only the first end is rigidly secured to the lower seal ring.

It is also another object of the present invention to provide a seal assembly including a retractor extending from the seal cap.

It is still another object of the present invention to provide a seal assembly wherein the housing further includes an attachment ring detachably secured to the lower seal ring for permitting selective attachment of the retractor by positioning it between the attachment ring and the lower seal ring.

It is yet another object of the present invention to provide a seal assembly where an upper end of the seal is connected to the upper seal ring and a lower end of the seal is connected to the lower seal ring.

It is a further object of the present invention to provide a seal assembly including an ergonomic cover member secured to the upper seal ring, wherein the ergonomic cover member includes a contoured outer surface providing for improved handling and twisting of the upper seal ring for opening and closing the seal.

It is another object of the present invention to provide a seal assembly wherein the seal is an iris seal.

It is also an object of the present invention to provide a seal assembly wherein the iris seal is constructed in a folded configuration spanning the upper seal ring and the lower seal ring.

It is still another object of the present invention to provide a seal assembly wherein the iris seal is composed of a rubber like member.

It is also an object of the present invention to provide a seal assembly including a contoured ring secured to the upper seal ring, the contoured ring including an inner circumference formed with a series of recesses shaped and dimensioned for receiving fingers of a user.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

Figure 1:
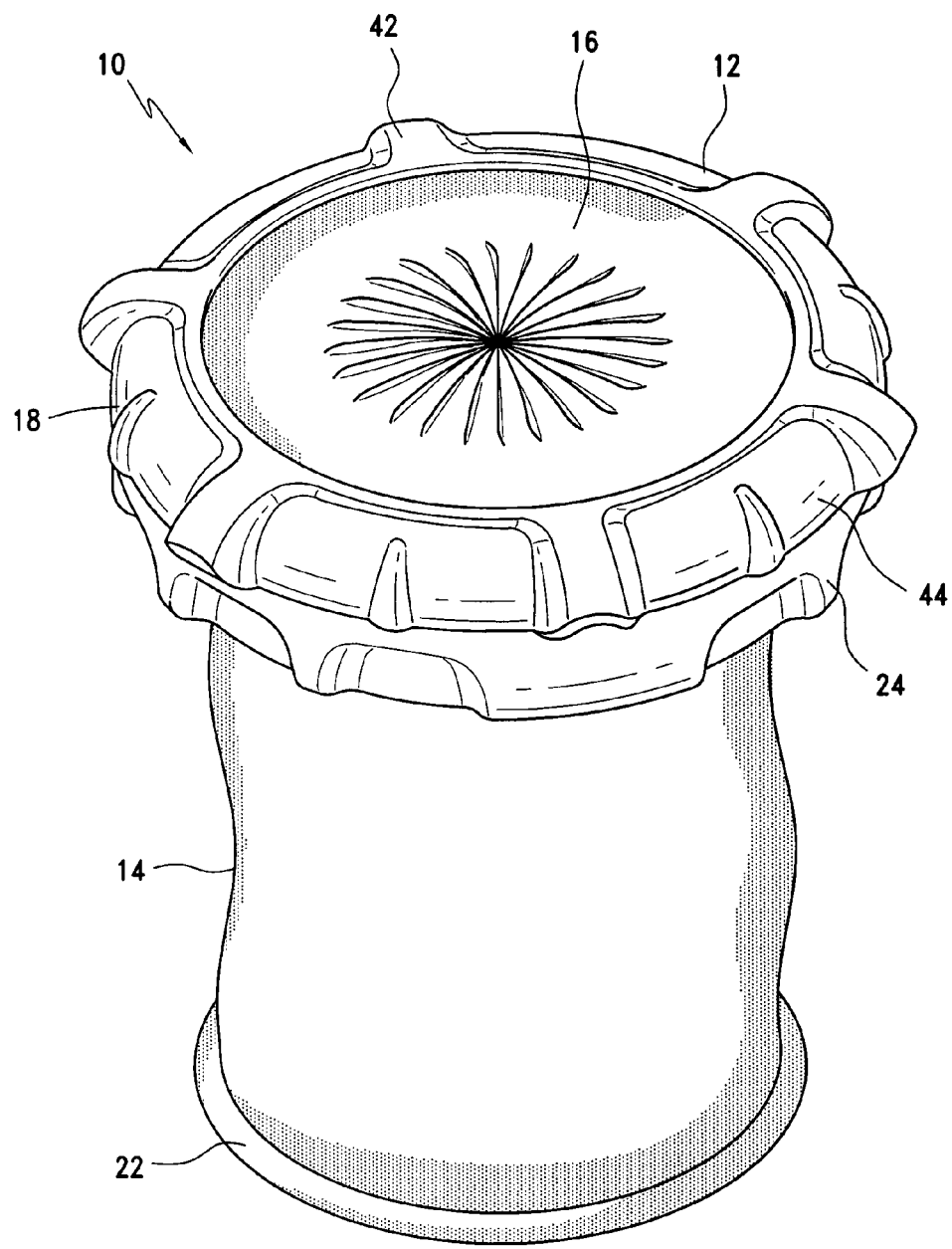
FIG. 1 is a perspective view of the present hand assisted laparoscopic seal assembly.
Figure 2:
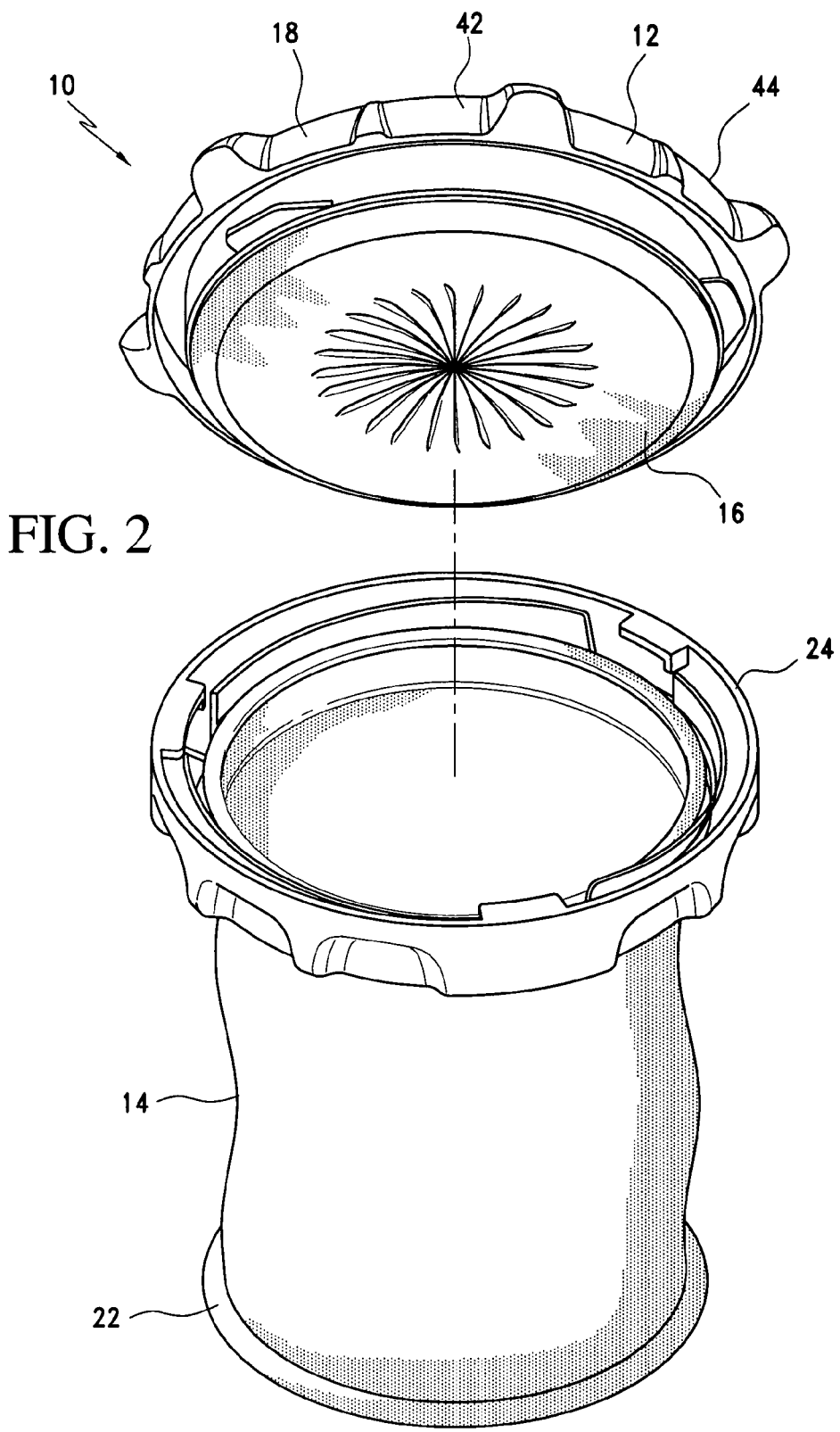
FIG. 2 is a perspective view of the hand assisted laparoscopic seal assembly with the attachment ring and retractor disengaged from the seal cap.
Figure 3:
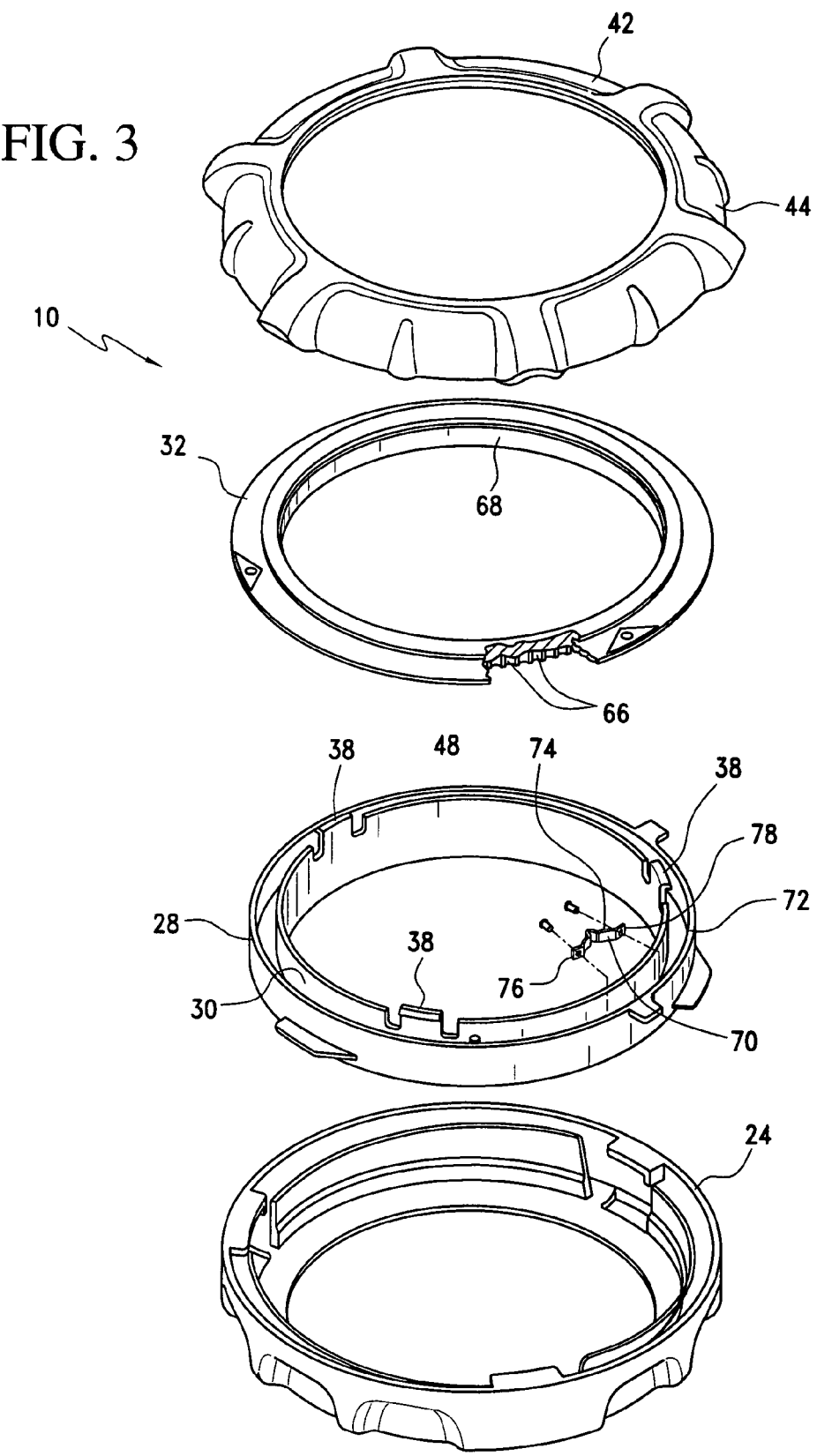
FIG. 3 is an exploded view of the seal cap of the present seal assembly.
Figure 4:
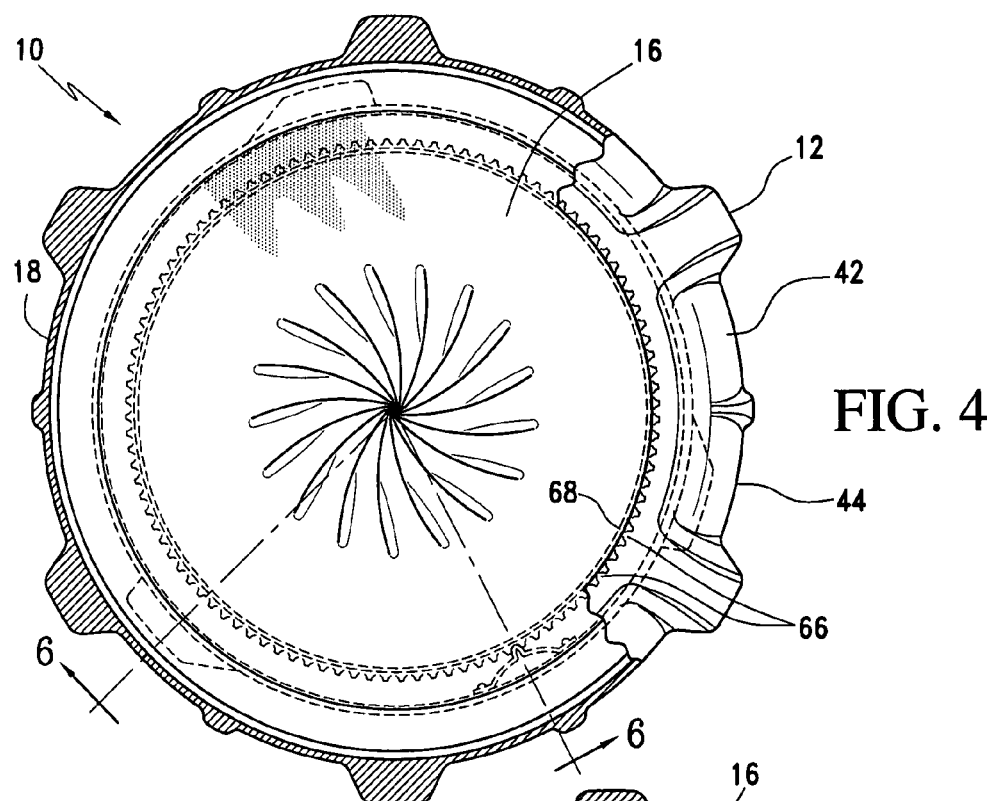
FIGS. 4 and 5 are partial sectional top views showing actuation of the present hand assisted laparoscopic seal assembly respectively between a closed and an open orientation.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Referring to FIGS. 1 to 8, a seal assembly 10 for permitting hand assisted laparoscopic procedures is disclosed. The seal assembly 10 generally employs an iris seal cap 12 and retractor 14 to ensure abdominal pressure is not compromised during hand exchanges while hand assisted laparoscopic procedures are performed. As such, and in accordance with a preferred embodiment of the present invention, the seal assembly 10 includes an iris seal 16 housed within a seal cap 12. The iris seal 16 includes a central access opening 46 allowing access to the body cavity as desired by the surgeon, or other medical practitioner, performing the procedure. As a result, the iris seal 16 is shaped and dimensioned to create a gas tight barrier around the surgeon's wrist when inserted through the seal assembly 10 and also creates a gas tight barrier between the interior abdominal space and the external environment when a hand is not inserted through the seal assembly 10. As will be discussed below in greater detail, adjustment of the iris seal 16, and ultimately the central access opening 46, provides for access to the body cavity in this highly controlled manner.

Referring to the various figures, the seal cap 12 includes an iris seal 16 positioned within a housing 18. The housing 18 is made of soft textured material such as the thermoplastic elastomer SANTOPRENE, or other like materials, and supports the iris seal 16 in a concentric manner.

As with prior hand assisted laparoscopic seal assemblies, the housing 18 of the present seal assembly 10 is secured to the abdominal wall 20 of an individual patient by first creating an incision and positioning the retractor 14 above the incision. Thereafter, the retractor 14, which will eventually be coupled to the seal cap 12, is inserted into the body cavity with the abdominal wall 20 therebetween. The seal cap 12 is then connected to the retractor 14 in a manner securely connecting and supporting the seal cap 12 on the outside of the abdominal wall 20 with the abdominal wall 20 resiliently held between the retractor 14 and the seal cap 12.

More particularly, the surgical site is prepared in accordance with conventional standard hospital procedures, making sure the skin is clean and dry. Thereafter, a template is placed over the incision site and an incision line is marked upon the template using a sterile skin marker. As those skilled in the art will appreciate, the glove size dictates the size of the incision. For example, if the surgeon's glove size is 7, a 6.5 to 7.0 cm incision is usually appropriate. Thereafter, an incision is made along the marked incision line. The incision size is thereafter verified by inserting the surgeon's hand into the abdomen prior to installing the retractor 14 and present seal cap 12. If the incision is too small, the incision is extended as required on each end to maintain the central position of the incision relative to the placement of the retractor 14 and present seal assembly 10. Thereafter, the lower retractor ring 22 of the retractor 14 is inserted through the incision. Using one's fingers, the retractor 14 is seated evenly under the peritoneum and the area is swept to ensure the retractor 14 is not lying between tissue layers. Thereafter, the seal cap 12 is attached to the retractor 14 via an attachment ring 24, which may be rigid but not limited thereto, and adjustments are made to ensure the seal assembly 10 is secured with the patient's abdomen, maintaining pneumo. As those skilled in the art will certainly appreciate, the retractor may be a fixed length or adjustable length retractor. In either case the retractor 14 must fit the abdominal wall thickness to maintain stability and pneumo. As briefly discussed above, the present seal assembly 10 is provided with an attachment ring 24 that is detachable from the remaining portions of the housing 18 for permitting selective attachment of the retractor 14 to the present seal cap 12. In accordance with a preferred embodiment, the attachment ring is that disclosed in commonly owned U.S. patent application Ser. No. 11/607,118, entitled "Hand Assisted Laparoscopic Device", filed Dec. 1, 2006, which is incorporated herein by reference, although other retractor attachment structures may be employed without departing from the spirit of the invention.

In accordance with a preferred embodiment, the iris seal 16 is a rotatable seal which selectively opens to permit passage of a surgeon's hand therethrough and closes in a manner creating a gas tight barrier between the interior abdominal space and the external environment whether or not a hand or instrument 26 is inserted through the seal assembly 10. In particular, the housing 18 in which the iris seal 16 is supported includes a lower seal ring 28 having a track 30 which supports an upper seal ring 32 for relative rotational motion in a manner discussed below in greater detail.

As will be discussed below in greater detail, the upper end 34 of the iris seal 16 is permanently connected to the upper seal ring 32. The lower end 36 of the iris seal 16 is permanently connected to the lower seal ring 28. The upper seal ring 32 and the lower seal ring 28 are connected together for relative rotational movement in a manner allowing for opening and closing of the iris seal 16. In accordance with a preferred embodiment, the upper seal ring 32 and the lower seal ring 28 are connected by at least three snap tabs 38 located on the lower seal ring 28 that are shaped and dimensioned to engage a recess 40 along the inner edge of the upper seal ring 32.

An ergonomic cover member 42 is secured to the upper seal ring 32. The ergonomic cover member 42 includes a contoured outer surface 44 providing for improved handling and twisting of the upper seal ring 32 relative to the lower seal ring 28 for opening and closing the iris seal 16 in accordance with the present invention. In accordance with a preferred embodiment, the ergonomic cover member 42 is a separate component fixedly secured to the upper seal ring 32 such that rotational force applied to the ergonomic cover member 42 is transmitted onto the upper seal ring 32 for opening and closing of the iris seal 16 by rotating the upper seal ring 32 relative to the lower seal ring 28. However, and as those skilled in the art will certainly appreciate, the ergonomic cover member could be integrally formed with the upper seal ring, while still remaining within the spirit of the present invention.

Referring to FIGS. 4, 5, 6 and 7, as discussed below in greater detail, the iris seal 16 is secured between the upper seal ring 32 and the lower seal ring 28. The upper seal ring 32 is supported within a track 30 of the lower seal ring 28 in a manner facilitating rotational movement between the upper seal ring 32 and the lower seal ring 28. In this way, the rotational movement of the upper seal ring 32 relative to the lower seal ring 28 is utilized to control the opening and closing of the iris seal 16 for one-hand insertion of a hand through the present seal assembly 10.

Figure 5:
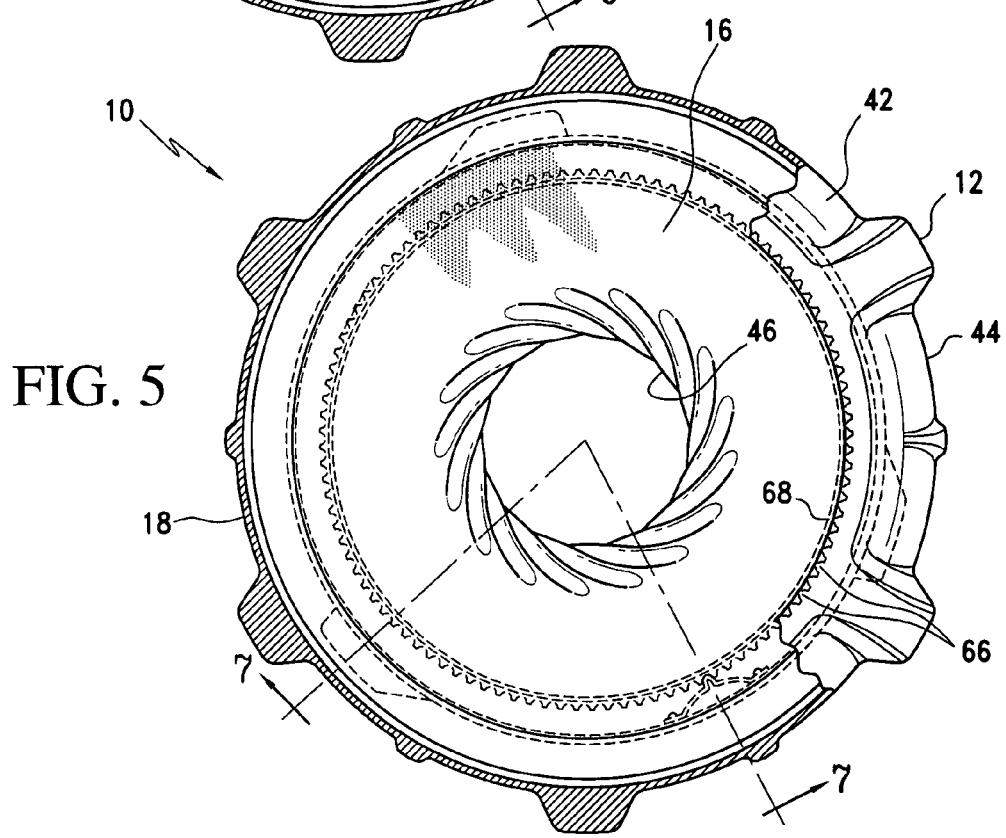
Figure 6:
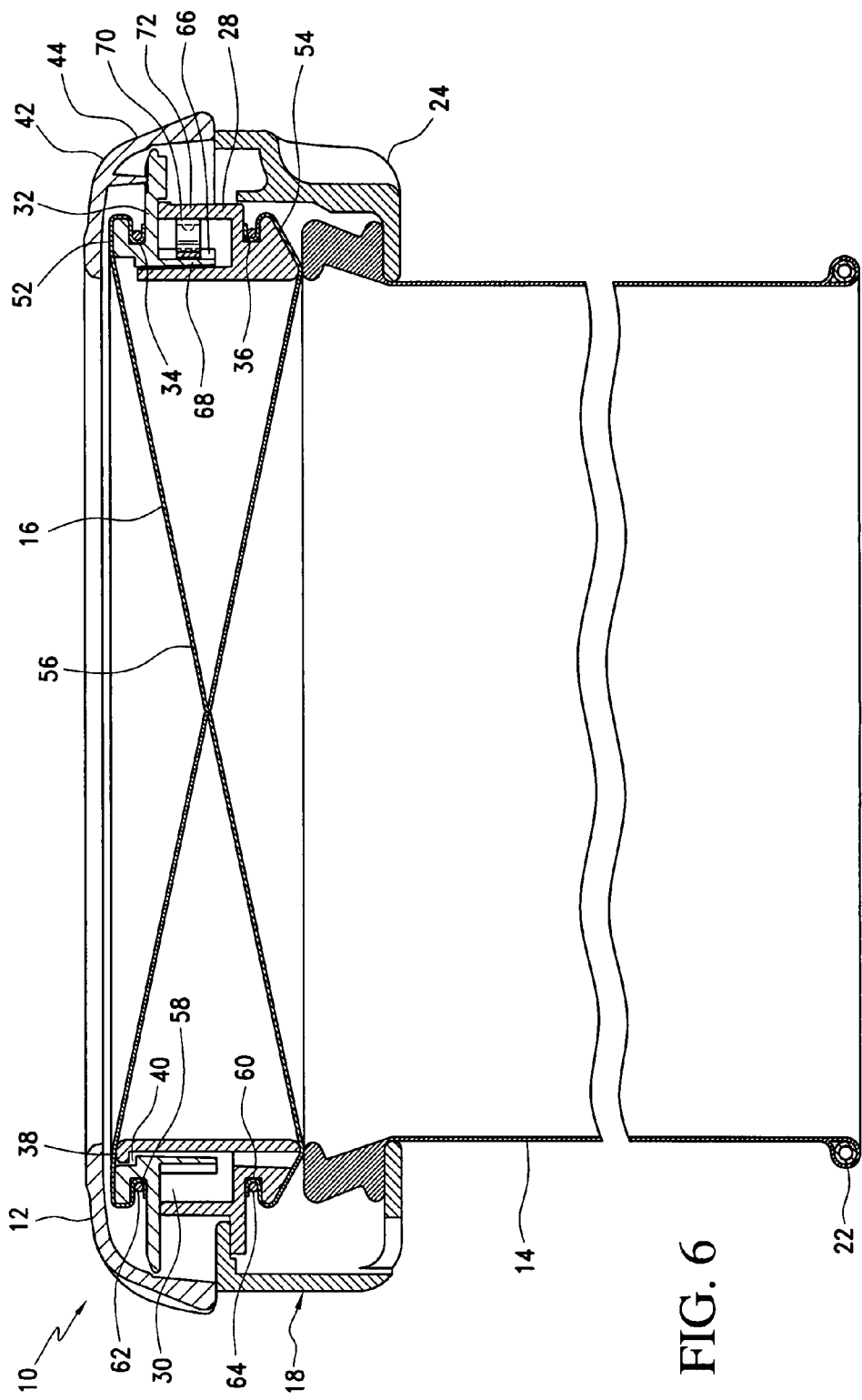
FIG. 6 is cross sectional view taken along the line 6-6 in FIG. 4.
Figure 7:
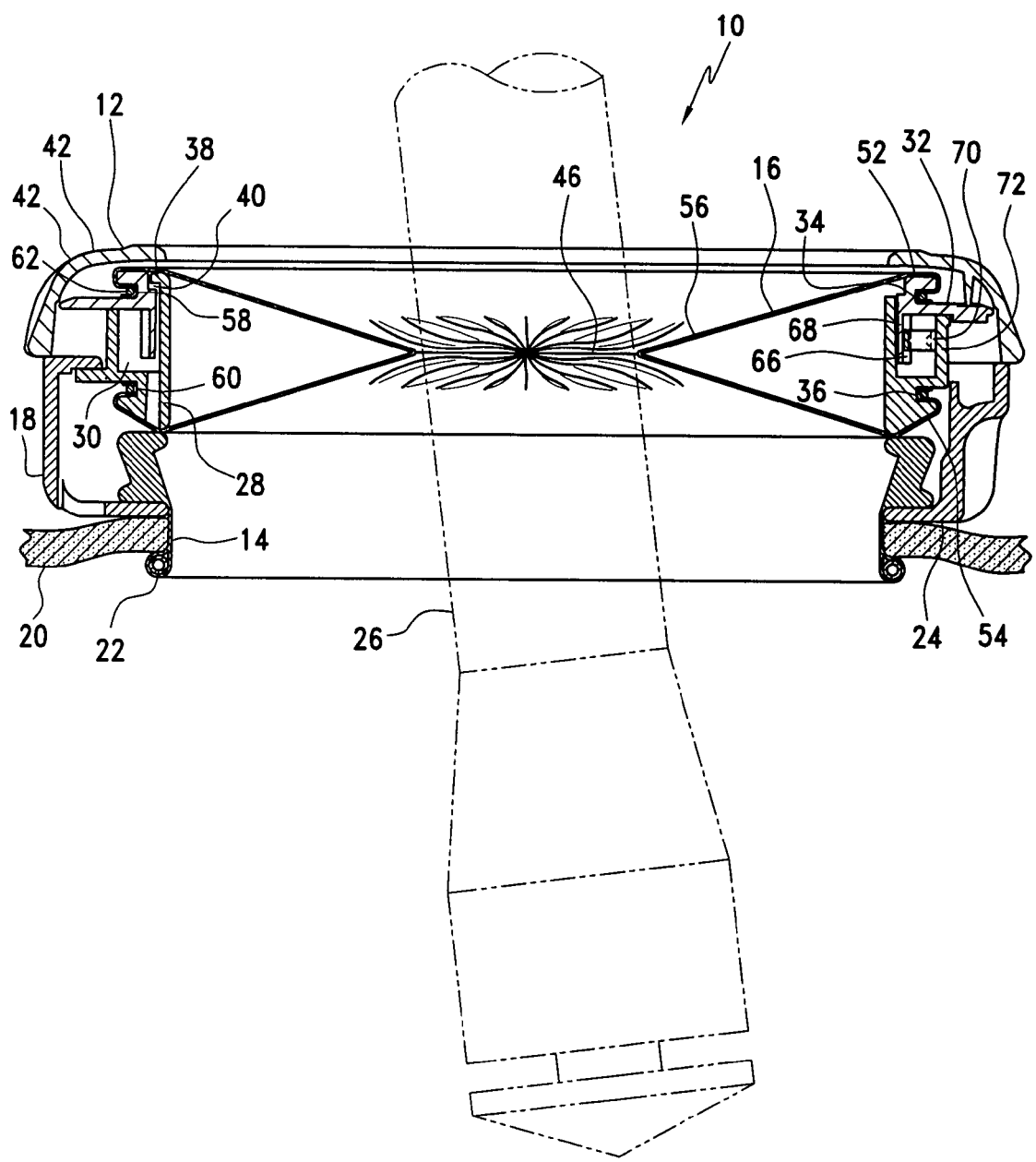
FIG. 7 is cross sectional view taken along the line 7-7 in FIG. 5 with an instrument shown in phantom.
Figure 8:
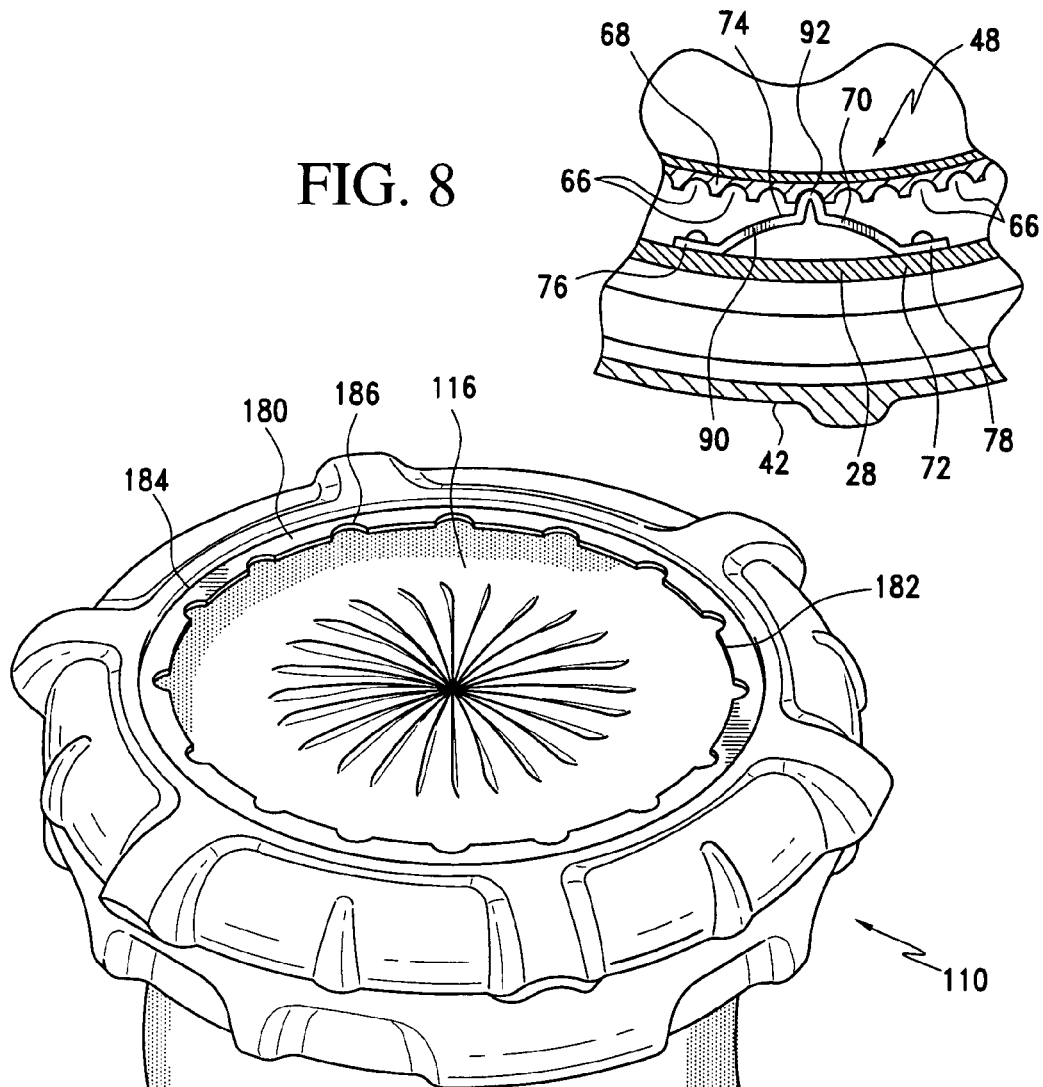
FIG. 8 is a cross sectional view of the present ratchet mechanism.

The iris seal 16 is mounted between the upper seal ring 32 and the lower seal ring 28 such that upon rotation of the upper seal ring 32 relative the lower seal ring 28 in a predetermined direction, the central access opening 46 of the iris seal 16 will open providing a surgeon with a central access opening 46 for passage of his hand therethrough. After the upper seal ring 32 is released, the upper seal ring 32, and ultimately, the iris seal 16 will rotate in the reverse direction, under the control of the ratchet mechanism 48 and at least one deflection feature, such as, flat spring 74 (as disclosed in accordance with a preferred embodiment) biasing the upper seal ring 32 relative to the lower seal ring 28, the central access opening 46 will close securely about the wrist of the surgeon or instrument. That is, the upper seal ring 32 and the iris seal 16 are moved between an open orientation (see FIGS. 5 and 7) in which a central access opening 46 is created within the iris seal 16 and a closed orientation (see FIGS. 4 and 6) in which the iris seal 16 is either wrapped about the wrist of a user with his or her hand inserted therein or substantially fully closed when the iris seal 16 is not in use. Although FIGS. 5 and 7 show the iris seal 16 in a partially opened orientation sufficient for passing a hand therethrough when sealing thereabout is desired, those skilled in the art will appreciate the upper seal ring 32 and the lower seal ring 28 may be rotated further relative each other creating a fully opened orientation for viewing within the cavity or insertion of an instrument or hand therethrough.

Opening and closing of the iris seal 16 is achieved by constructing the iris seal 16 in a folded configuration spanning the upper seal ring 32 and the lower seal ring 28 in a substantially taut configuration. As such, rotation of the upper seal ring 32 relative to the lower seal ring 28 in a first direction will result in an increase of tension along the iris seal 16 in a manner drawing the fold outwardly opening the central access opening 46 in the iris seal 16.

In accordance with a preferred embodiment, the iris seal 16 is composed of a rubber like member. The rubber like member is constructed in the shape of a cylindrical section with the upper and lower sections 52, 54 thereof having a wider diameter than the central section 56 (thereby offering a cross section as shown in FIGS. 6 and 7). As will be appreciated based upon the following disclosure, the construction of the rubber like member creates a substantially planar iris seal 16 which is closed or opened when the upper seal ring 32 and the lower seal ring 28 are rotated relative to one another in opposite directions.

In accordance with a preferred embodiment, the rubber like member is formed from a thin film having a thickness less than 0.025" and made from a material having elasticity, such as, natural rubber, synthetic rubber, poly vinyl chloride, silicon and a variety of elastomers (for example, urethane, polyisoprene, silicone). As briefly mentioned above, the rubber like member is cylindrical and includes a central access opening 46 having a predetermined cross sectional area at the central section 56 thereof. The rubber like member is shaped such that the diameter of the opening decreases in the direction from the upper and lower sections to the central section 56 of the rubber like member. Furthermore, the upper and lower ends 34, 36 of the iris seal 16, which are fitted into the grooves 58, 60 of the upper seal ring 32 and the lower seal ring 28 and held therein with O-rings 62, 64, allow for detachment from the upper seal ring 32 and the lower seal ring 28. In accordance with a preferred embodiment, the O-rings are integrated into the iris seal 16, minimizing components and material cost. Because of such detachable structure of the rubber like member, it can be easily replaced by a fresh member when the used rubber like member is broken or worn. This technique would be useful for reusable devices.

As briefly discussed above, FIGS. 4, 5, 6 and 7 present a plan view and a sectional view showing the iris seal 16 in its respective closed and open states. FIGS. 5 and 7 show the iris seal 16 in an open state for inserting a hand or instrument therethrough when sealing is desired. This open state is created when the upper seal ring 32 is rotated relative to the lower seal ring 28 at a predetermined angle, for example, 15 degrees, from the closed state of the iris seal 16, and the central access opening 46 is created. As mentioned above, further rotation would result in a larger opening that might be desirable for greater access.

Figure 9:
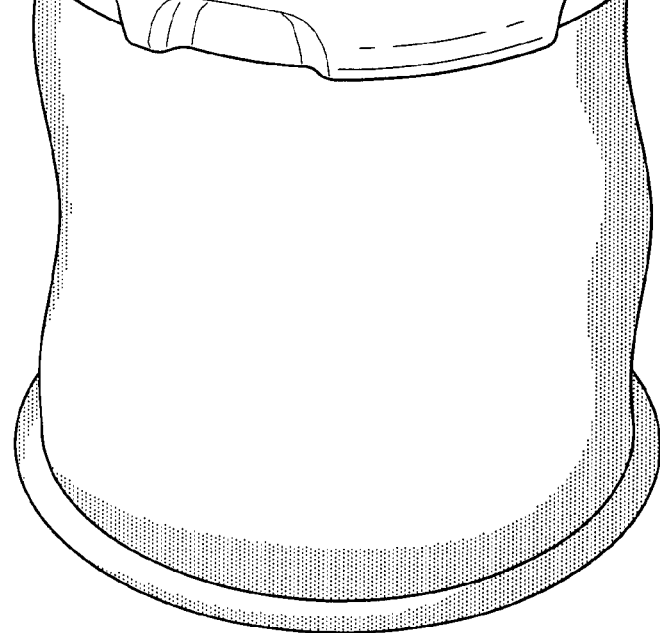
FIG. 9 is a perspective view of a hand assisted laparoscopic seal assembly in accordance with an alternate embodiment.

In accordance with an alternate embodiment, and with reference to FIG. 9, improved manual movement of the upper seal ring 32 relative to the lower seal ring 28, and ultimately, the iris seal 16, is achieved by the provision of a contoured ring 180 secured to the upper surface of the upper seal ring. The contoured ring 180 is substantially annular and includes an inner circumference 182 and an outer circumference 184. The outer circumference 184 is substantially smooth and conforms to the profile of the upper seal ring. However, the inner circumference 182 is formed with a series of recesses shaped and dimensioned for receiving the fingers of a medical practitioner attempting to use the present seal assembly 110. In particular, the recesses 186 are shaped and dimensioned such that an individual wishing to use the present seal assembly 110 may seat his or her fingers therein and rotate the contoured ring, and the upper seal ring to which the contoured ring 180 is rigidly attached, and ultimately the iris seal 116 with only one hand. While the iris seal 116 is in its open orientation, the user may simply slip his or her hand through the iris seal 116 and proceed with the surgical procedure with minimal loss of insufflation. This feature allows the physician's other hand to be free and undisrupted, allowing the surgeon to maintain his procedural focus and position with the free hand during hand exchanges.

As some surgeons may want to maintain an open orientation using the ratchet mechanism 48, a mechanism for controlled closure position of the present seal assembly 10 has been developed. In accordance with a first embodiment, a ratchet mechanism 48 has been developed wherein the surgeon needs control over the upper seal ring 32 relative to the lower seal ring 28 and iris seal 16 from its open orientation to its closed orientation.

In accordance with a preferred embodiment, and with reference to FIGS. 3, 4, 5, 6, 7 and 8, the upper seal ring 32 is seated within the track 30 of the lower seal ring 28 and the upper seal ring 32 relative to the lower seal ring 28 for movement relative thereto assisting in opening the iris seal 16 to open and close the central access opening 46 in a controlled manner. However, the ratchet mechanism 48 is positioned between the upper seal ring 32 and the lower seal ring 28. The ratchet mechanism 48 includes a series of gear teeth 66 secured to a downwardly extending flange 68 extending downwardly from the upper seal ring 32. The gear teeth 66 are oriented to engage an inwardly facing spring fastener(s) 70 secured to an upwardly extending wall 72 of the lower seal ring 28. Interaction between the gear teeth 66 and the spring fasteners 70 functions to hold the upper seal ring 32 relative to the lower seal ring 28 in a controlled manner as it is moved to an open orientation.

In accordance with a preferred embodiment, the slope of the gear teeth 66 formed along the downwardly extending flange 68 of the upper seal ring 32 are optimized to prevent auto opening when the hand is inserted into the device. However, the slopes do permit opening and closing in a highly controlled manner optimizing functioning of the present seal assembly 10. As with the gear teeth 66, the spring fastener 70 is shaped and dimensioned to optimize its ability to hold and maintain the iris seal, and ultimately the upper and lower seal members at desired positions.

The spring fastener 70 is composed of a flat spring 74 (may be called a leaf spring also) having first and second ends 76, 78 rigidly secured to the lower seal ring 28 in a manner facing the gear teeth 66 of the upper seal ring 32. Between the first and second ends 76, 78 of the flat spring 74 is a substantially convex portion 90 having a central protrusion 92 which is shaped and dimensioned to seat within the gear teeth 66 as the upper and lower seal rings 32, 28 are moved relative to each other.

Figure 10:
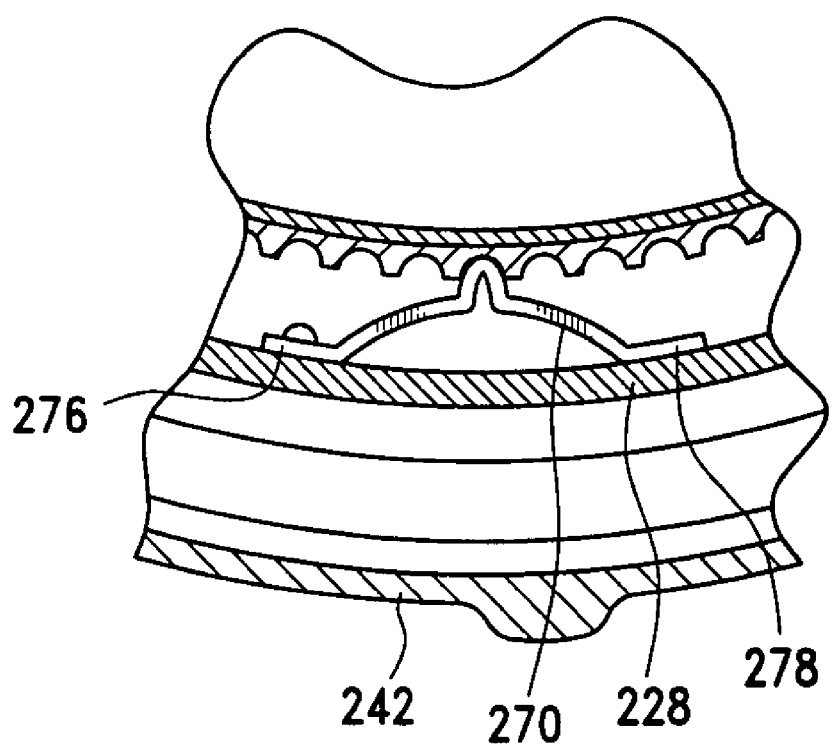
FIG. 10 is a cross sectional view of an alternate embodiment of the ratchet mechanism.

Although the spring fastener is disclosed above as being secured to the lower seal ring along both its first and second ends, it is contemplated the spring fastener 270 may be varied as shown in FIG. 10 such that only the first end 276 of the spring fastener 270 is secured to the lower seal ring 228. This would allow for the second end 278 to freely move relative to the lower seal ring 228. While this embodiment is disclosed with the first end secured and the second end free, those skilled in the art will appreciate this could certainly be altered such that the first end is free and the second end is secured.

In accordance with a preferred embodiment, the flat spring 74 is composed of a metal, such as, stainless steel. It may also be configured using plastic, such as, polypropylene, so that the deflection is not beyond the yield strength of the material. While preferred materials are discussed herein, those skilled in the art will appreciate that a variety of materials may be used without departing from the spirit of the present invention. In addition, the spring bias of the flat spring 74 is determined such that when rotating the iris seal 16 the flat spring 74 and the gear teeth 66 must be able to hold the reactive force (torque). This requires the flat spring 74 to hold that force. The iris seal 16 material properties and thickness is the major contributor to this force. Typical loading is approximately 25 in*lbs of torque (torque can be converted into a force by dividing it by the iris seals outer diameter), which required to move the upper seal ring 32 relative to the lower seal ring 28.

Alternate means of engaging the gear teeth other than a flat spring can be used to create the same output of one moving the ring to overcome the spring. Overcoming the spring is by deflection of the flat spring. Other means are possible such as those used in socket wrenches causing deflection of a spherical ball that is deflected outward by a spring.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A seal assembly for permitting hand assisted laparoscopic procedures, comprising:
    a seal cap including a seal positioned within a housing, the housing including a lower seal ring having a track which supports an upper seal ring for relative rotational motion, wherein the seal is constructed in the shape of a cylindrical section, the seal includes an upper section and a lower section with a central section therebetween, the upper section of the seal is coupled to the upper seal ring and the lower section of the seal is coupled to the lower seal ring, the seal being supported between the upper seal ring and the lower seal ring for rotation between an open orientation and a closed orientation;
    a ratchet mechanism controlling motion of the upper seal ring relative to the lower seal ring, the ratchet mechanism includes a deflection feature and a series of gear teeth, wherein the series of gear teeth are oriented to engage the deflection feature; and
    wherein the deflection feature is a spring fastener and the spring fastener is a flat spring having a first end rigidly secured to one of the lower seal ring or the upper seal ring and a second end rigidly secured to one of the lower seal ring or the upper seal ring.

2. The seal assembly according to claim 1, wherein the series of gear teeth is secured to the upper seal ring and the deflection feature is secured to the lower seal ring.

3. The seal assembly according to claim 2, wherein the upper seal ring includes a downwardly extending flange and the series of gear teeth is secured to the downwardly extending flange, and the lower seal ring includes an upwardly extending wall and the deflection feature is secured to the upwardly extending wall.

4. The seal assembly according to claim 1, wherein the spring fastener includes a convex portion between the first end and the second end, and the convex portion is shaped and dimensioned to seat within the series of gear teeth as the upper seal ring and the lower seal ring are moved relative to each other.

5. The seal assembly according to claim 1, further including a retractor extending from the seal cap.

6. The seal assembly according to claim 1, where an upper end of the seal is connected to the upper seal ring and a lower end of the seal is connected to the lower seal ring.

7. The seal assembly according to claim 1, wherein the seal is an iris seal.

8. The seal assembly according to claim 7, wherein the iris seal is constructed in a folded configuration spanning the upper seal ring and the lower seal ring.

9. A seal assembly for permitting hand assisted laparoscopic procedures, comprising:
    a seal cap including a seal positioned within a housing, the housing including a lower seal ring having a track which supports an upper seal ring for relative rotational motion, wherein the seal is constructed in the shape of a cylindrical section, the seal includes an upper section and a lower section with a central section therebetween, the upper section of the seal is coupled to the upper seal ring and the lower section of the seal is coupled to the lower seal ring, the seal being supported between the upper seal ring and the lower seal ring for rotation between an open orientation and a closed orientation;
    a ratchet mechanism controlling motion of the upper seal ring relative to the lower seal ring, the ratchet mechanism includes a deflection feature and a series of gear teeth, wherein the series of gear teeth are oriented to engage the deflection feature; and
    wherein the deflection feature is a spring fastener and the spring fastener is a flat spring having a first end and a second end and the spring fastener includes a convex portion between the first end and the second end, and the convex portion is shaped and dimensioned to seat within the series of gear teeth as the upper seal ring and the lower seal ring are moved relative to each other; wherein only the first end of the spring fastener is rigidly secured to the lower seal ring.

10. The seal assembly according to claim 9, wherein the series of gear teeth is secured to the upper seal ring and the deflection feature is secured to the lower seal ring.

11. The seal assembly according to claim 10, wherein the upper seal ring includes a downwardly extending flange and the series of gear teeth is secured to the downwardly extending flange, and the lower seal ring includes an upwardly extending wall and the deflection feature is secured to the upwardly extending wall.

12. A seal assembly for permitting hand assisted laparoscopic procedures, comprising:
    a seal cap including a seal positioned within a housing, the housing including a lower seal ring having a track which supports an upper seal ring for relative rotational motion, wherein the seal is supported between the upper seal ring and the lower seal ring for rotation between an open orientation and a closed orientation;

a ratchet mechanism controlling motion of the upper seal ring relative to the lower seal ring, the ratchet mechanism includes a deflection feature and a series of gear teeth, wherein the series of gear teeth are oriented to engage the deflection feature; and wherein the deflection feature is a spring fastener and the spring fastener is a flat spring having a first end and a second end and the spring fastener includes a convex portion between the first end and the second end, and the convex portion is shaped and dimensioned to seat within the series of gear teeth as the upper seal ring and the lower seal ring are moved relative to each other;

wherein the series of gear teeth is secured to the upper seal ring and the deflection feature is secured to the lower seal ring, the upper seal ring including a downwardly extending flange and the series of gear teeth is secured to the downwardly extending flange, and the lower seal ring includes an upwardly extending wall and the deflection feature is secured to the upwardly extending wall, and wherein the first end and the second end of the spring fastener are rigidly secured to the lower seal ring.

13. A seal assembly for permitting hand assisted laparoscopic procedures, comprising:

a seal cap including a seal positioned within a housing, the housing including a lower seal ring having a track which supports an upper seal ring for relative rotational motion, wherein the seal is supported between the upper seal ring and the lower seal ring for rotation between an open orientation and a closed orientation;

the seal is constructed in the shape of a cylindrical section, the seal includes an upper section and a lower section with a central section therebetween, the upper section of the seal is coupled to the upper seal ring and the lower section of the seal is coupled to the lower seal ring; and a ratchet mechanism controlling motion of the upper seal ring relative to the lower seal ring wherein the ratchet mechanism includes a deflection feature and a series of gear teeth, wherein the series of gear teeth are oriented to engage the deflection feature; wherein the deflection feature is a spring fastener and the spring fastener is a flat spring having a first end rigidly secured to one of the lower seal ring or the upper seal ring and a second end rigidly secure dot one of the lower seal ring or the upper seal ring.

14. The seal assembly according to claim 13, wherein the seal is an iris seal.

15. The seal assembly according to claim 13, wherein the upper seal ring includes a groove and the upper section of the iris seal is fitted into the groove and the lower seal ring includes a groove and the lower section of the iris seal is fitted into the groove.

16. The seal assembly according to claim 15, further including an O-ring holding the upper section of the iris seal within the groove of the upper seal ring and an O-ring holding the lower section of the iris seal within the groove of the lower seal ring.

17. The seal assembly according to claim 13, wherein the upper section of the seal has a first diameter, the lower section of the seal has a second diameter and the central section of the seal has a third diameter, and wherein the first diameter and second diameter are wider than the third diameter.

* * * * *